United States Patent [19]

Botka et al.

[11] Patent Number: 5,587,611
[45] Date of Patent: Dec. 24, 1996

[54] COPLANAR X-RAY PHOTODIODE ASSEMBLIES

[75] Inventors: Alexander T. Botka, Cambridge, Vt.; Ben Tuval, Brookline; Sorin Marcovici, Lexington, both of Mass.

[73] Assignee: Analogic Corporation, Peabody, Mass.

[21] Appl. No.: 436,572

[22] Filed: May 8, 1995

[51] Int. Cl.$^6$ .................. H01L 27/146; H01L 31/075; H01L 31/115

[52] U.S. Cl. .................. 257/458; 257/446; 257/464; 250/370.09; 250/370.11; 250/370.14

[58] Field of Search .................. 257/458, 446, 257/464; 250/370.09, 370.11, 370.14

[56] References Cited

U.S. PATENT DOCUMENTS 4,282,541  8/1981  Tsang .................................. 257/458
4,914,301  4/1990  Akai .................................. 250/370.11
5,360,987  11/1994  Shibib .................................. 257/458
5,465,002  11/1995  Snoeys .................................. 257/458

OTHER PUBLICATIONS

Promod Hague, "Scintillator crystal–photodiode array detectors" in Thomas H. Newton and D. Gordon Potts (eds.), *Technical Aspects of Computed Tomography*, vol. 5 at 4127–4132 (1981). no month.

Primary Examiner—Jerome Jackson
Attorney, Agent, or Firm—Lappin & Kusmer

[57] ABSTRACT

A coplanar photodiode construction is disclosed having particular utility in X-ray detection applications in which alternating P-doped and N-doped regions, separated by undoped material, are located in relatively shallow depth under and along the surface between the photodiode and an associated X-ray scintillating crystal.

40 Claims, 3 Drawing Sheets

COPLANAR X-RAY PHOTODIODE ASSEMBLIES

This invention relates generally to an improved X-ray photodiode, to multi-element arrays of such diodes for use in connection with X-ray detection apparatus, and to an improved X-ray detection system employing the improved photodiodes of this invention.

BACKGROUND OF THE INVENTION

X-ray detection systems for such applications as computerized tomography commonly employ combinations of scintillating crystals and photodiodes. For example, a CAT scanner system operates by taking multiple, cross-sectional, X-ray slices from different angles within a single plane passing through a body. An X-ray source and an array of detectors are placed on opposite sides of an annular gantry, which rotates in the selected plane around the body. Signals generated by the detector array are digitized and mathematically processed to create a cross-sectional image of the body.

In a scintillating-photodiode X-ray detection system, the incident X-rays are absorbed by a scintillating crystal and converted into visible light. That visible light is then absorbed into a silicon photodiode, which converts the light into electron-hole pairs that diffuse from the P-N junction and thereby could generate a current flow. Because the current flow is typically of very small magnitude, it is common to use an amplification means to amplify the photodiode signal and convert it into a voltage. The output of such a scintillating-photodiode-preamplifier system is a voltage that is proportional in magnitude to the incident X-ray flux on the scintillating crystal. Systems of this type are described in a chapter by Promod Hague entitled "Scintillator crystal-photodiode array detectors" appearing in Thomas H. Newton and D. Gordon Potts (eds.), "Technical Aspects of Computed Tomography," vol. 5 at 4127–4132 (1981), which chapter is incorporated herein by reference.

In a typical photodiode construction, the silicon wafer is appropriately doped so as to create a narrow P-type zone or region adjoining a first face of the wafer and a narrow N-type zone adjoining a second, opposite face, the P and N zones being separated by an almost intrinsic region in the interior portion of the wafer. For example, it is conventional to create P-type zones using a boron dopant and N-type zones using a phosphorus dopant. The photodiode is mounted on a substrate, for example, along the N-type face, and a scintillating crystal is mounted along the P-type face using silicon grease or other optically-transparent epoxy as a coupling medium between the adjoining scintillating crystal and photodiode surfaces. Electrical terminals are connected respectively to the P and N zones to collect the current flow generated by the photodiode.

The conventional photodiode construction described above is generally well suited for detecting light in the infrared range because these light photons generate electron-hole pairs at internal locations relatively distant from the surface. Thus, accurate readings of infrared radiation require that electrical charge be collected over much of the internal volume of the silicon. By contrast, it is well known that X-ray scintillating crystals typically produce blue light photons having a wavelength of about one-half that of infrared radiation. Unlike infrared light, the blue light photons penetrate on the order of only several microns into the silicon. Accordingly, for such X-ray detection applications, applicants have found that it is only necessary to collect the light-generated electrical charge from the surface of the photodiode and from those internal regions immediately adjacent to the photodiode surface.

At the same time, however, because of the very low level of the electrical signals associated with X-ray detection applications, the familiar problems of "noise," "electrical cross-talk," "optical cross-talk" and "electrical response" become highly significant. "Electrical cross-talk" in this usage refers to a phenomenon that can occur in an array of multiple, adjacent scintillating crystal-photodiode pairs and their respective associated electrodes. If an electrical signal generated by an X-ray flux incoming to a first scintillating crystal-photodiode pair is accidentally "collected" at the electrodes associated with an adjacent scintillating crystal-photodiode pair, the result is an erroneous detection reading.

"Electrical response" here refers to the problem that a thicker electrical medium slows, reduces in magnitude, and may distort electrical signals passing through that medium. If a conventional X-ray photodiode construction is used for blue light photons, for example, an electrical signal generated in a 1–3 micron photodiode "depletion zone" adjacent to the scintillating crystal-photodiode interface would have to travel without recombination through as much as 300 microns of the silicon in order to reach the associated cathode terminal, thereby resulting in relatively slow and possibly inaccurate detection readings. It is, therefore, desirable to reduce the length of the electrical pathway that a generated electrical charge must traverse in order to reach the associated electrical terminal.

"Optical cross-talk" as used herein refers to the problem that a portion of the light photons generated in the scintillating crystal of a first scintillating crystal-photodiode pair may pass into a second, adjacent photodiode. Similarly, a light photon from a first scintillating crystal may be reflected off a metallized electrical contact, deflected into an adjacent crystal, and then directed into the photodiode associated with that adjacent crystal. The result in either case is the generation of an electrical charge in the second, adjacent photodiode instead of in the photodiode of the first scintillating crystal-photodiode pair, again resulting in a detection error. A related "noise" problem occurs when a portion of an X-ray flux to a scintillating crystal passes into an electrically-active zone of the silicon and generates charges by direct ionization of the silicon. Again, the result of the "noise" phenomenon could be an erroneous detection reading.

In addition to overcoming or minimizing the foregoing problems with conventional X-ray photodiodes and photodiode arrays, it is commercially desirable to produce X-ray photodiodes that are easier, faster and less expensive to make, and that have a higher degree of uniformity. These and other problems with and limitations of the prior art photodiode designs are largely overcome with the coplanar X-ray photodiodes, coplanar photodiode arrays, and coplanar photodiode X-ray detection systems of this invention.

OBJECTS OF THE INVENTION

Accordingly, it is a general object of this invention to provide coplanar X-ray photodiodes as well as photodiode arrays and X-ray detection systems utilizing such coplanar photodiodes.

A principal object of this invention is to provide a photodiode having an optimized geometry for the generation and collection of electrical charges along and in proximity to a single external surface of the photodiode.

A further object of this invention is to provide a photodiode having all electrical contacts along a single external surface of the photodiode.

Another object of this invention is to provide a coplanar photodiode assembly that is readily adaptable for use in an array of adjacent photodiodes for X-ray detection.

Still another object of this invention is to provide an array of adjacent coplanar photodiodes having reduced cross-talk effects.

Yet another object of this invention is to provide an X-ray detection system comprising an array of scintillating crystal and coplanar photodiode pairs.

An overall object of this invention is to provide X-ray detection systems having improved performance and lower production costs than comparable prior art systems by utilizing coplanar photodiodes and coplanar photodiode arrays according to this invention.

These and other objects and advantages of this invention will be better understood from the following description, which is to be read together with the accompanying drawings.

SUMMARY OF THE INVENTION

The coplanar photodiodes and coplanar photodiode arrays of this invention generally comprise silicon wafers having alternating P-doped and N-doped regions located in relatively shallow bands along a first wafer surface, and surrounded by regions of lightly-doped silicon. In any particular photodiode or photodiode array, either the P-doped or N-doped regions along the first wafer surface may predominate, as determined by the relative widths of the respective P and N bands. The silicon wafers of this invention may further comprise another doped region, of opposite polarity from the dominant polarity along the first wafer surface, and separated from the P and N regions along the first wafer surface by a lightly-doped silicon region. An X-ray detection system utilizing a photodiode array according to this invention is formed by gluing an X-ray scintillating crystal, using an optical epoxy, to the first wafer surface of each of the photodiodes such that a scintillating crystal is adjacent to and associated with each of the predominating P or N bands.

DETAILED DESCRIPTION OF THE INVENTION

Figure 1:
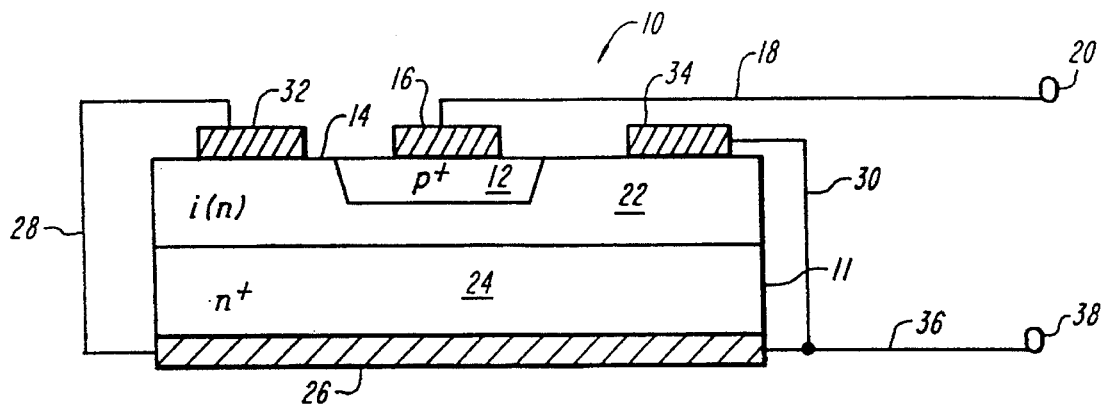
FIG. 1 is a schematic, sectional view illustrating an embodiment of a prior art X-ray detection photodiode, an embodiment which is not a part of or intended to be covered by this invention.

FIG. 1 schematically illustrates for comparison purposes a cross-section of a typical prior art PIN photodiode 10 used for infrared light detection applications. Photodiode 10 comprises a silicon wafer 11 having a P-doped (p+) region 12 along a first surface 14 of the silicon wafer. An electrical contact 16 is deposited on a surface portion of region 12 and connected by wire means 18 to an anode terminal 20. P-doped region 12 is surrounded by silicon bulk (i(n)) region 22. The side of wafer 11 opposite from the p+ region comprises an N-doped (n+) region 24 metallized with an electrically conductive layer 26. Wire means 28 and 30 respectively connect electrical contacts 32 and 34 on surface 14 to metallized layer 26, and wire means 36 connects metallized layer 26 to cathode terminal 38.

The detection apparatus of FIG. 1 is well suited for detecting infrared light because infrared light photons penetrate relatively deeply into the silicon wafer 11 and electrical charges are generated at locations relatively distant from the surface 14 where the light photons enter the wafer. X-ray detection systems, however, utilize solid state scintillating crystals comprising, for example, cadmium tungstate, cesium iodide, sodium iodide, bismium germanite, or the like, to convert X-rays into blue light for detection purposes. These conventional X-ray scintillating crystals do not convert X-rays into infrared light but rather into blue light photons having wavelengths of about 400–600 nm, which penetrate at most several microns into a silicon wafer. Thus, in X-ray detection, all electric charges are generated within a few microns, for example about 1–3 microns, of the surface where the blue light enters the silicon wafer. Because photodiodes are typically on the order of 300 microns in thickness, for X-ray detection applications only about the top 1–2% of the conventional photodiode serves any real purpose other than providing structural support for the surface region.

Figure 2:
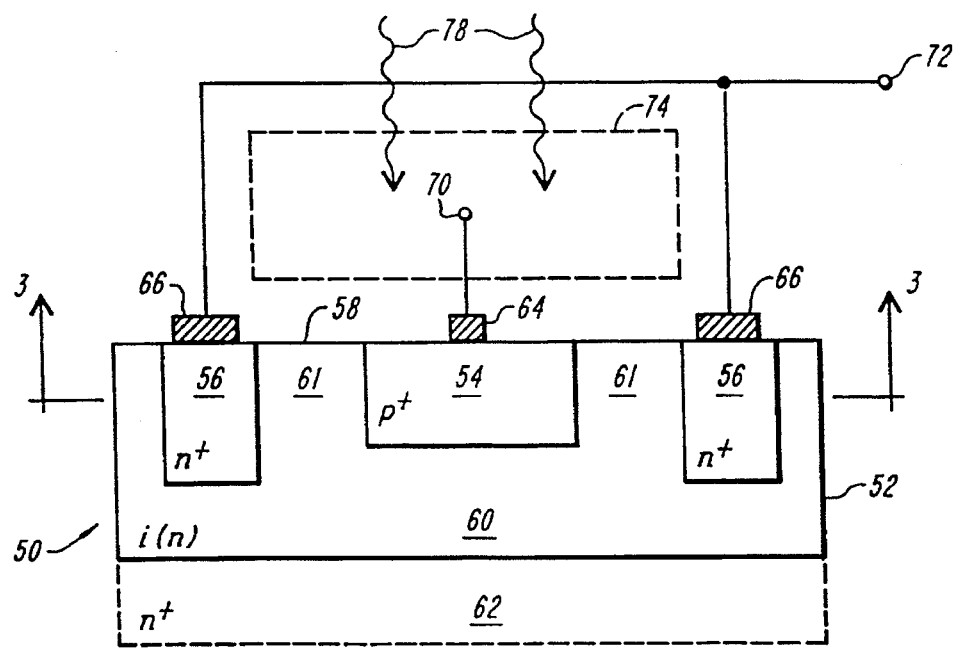
FIG. 2 is a schematic, sectional view illustrating an embodiment of a coplanar photodiode (or a portion of a coplanar photodiode array) in accordance with this invention.

By contrast, as seen in FIG. 2, the coplanar photodiodes of this invention are specially designed to efficiently detect the blue light generated by X-ray scintillating crystals. Coplanar photodiode 50 in accordance with one embodiment of this invention comprises a silicon wafer 52 having shallow, alternating bands of P-doped (p+) regions 54 and somewhat deeper N-doped (n+) regions 56 along and adjacent first planar surface 58 of the silicon wafer. P-doped regions 54 and N-doped regions 56 are formed into a silicon bulk (i(n)) region 60. Alternating bands of region 54 and region 56 are also separated by narrow bands 61 of the silicon bulk region 60 as shown in FIG. 2. In a preferred embodiment of this invention, regions 54 extend to a depth of about 1–2 microns from surface 58, whereas regions 56 extend to a depth of about 2–3 microns from surface 58. In a preferred embodiment of this invention, regions 54 range from about 800–1000 microns in width, regions 56 range from about 500–750 microns in width, and the bands 61 of region 60 separating adjacent bands of regions 54 and 56 range from about 10–25 microns in width.

Photodiode 50 illustrates a construction in which P-doped regions 54 predominate along surface 58, as seen by the relatively greater width of regions 54 as compared with N-doped regions 56. It will be understood that in an alternative and substantially equivalent embodiment of this invention, the predominant regions 54 may be N-doped, and regions 56 would then be P-doped. In still another embodiment, silicon wafer 52 may further comprise another N-doped region 62 underlying region 60 so as to create a silicon bulk region 60 between N-doped region 62 and the alternating P and N-doped regions 54 and 56 along wafer surface 58. It will also be understood that in the above-described alternative construction of the coplanar photodiode, wherein the predominant regions 54 are N-doped, underlying region 62 would be doped so as to have an opposite polarity (p+) from that of the predominant (n+) regions along surface 58.

Figure 3:
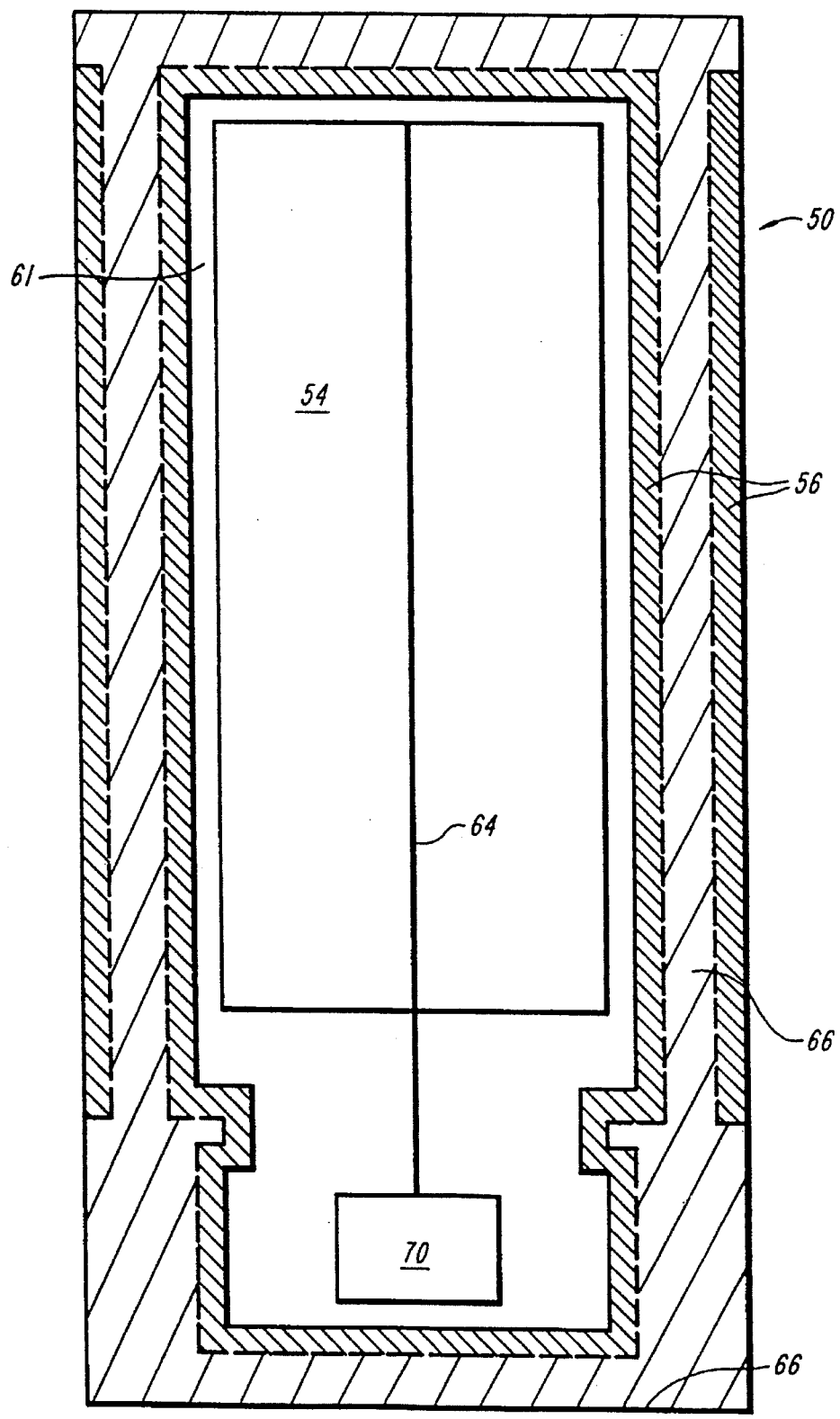
FIG. 3 is an enlarged, schematic sectional view along the line 3—3 of the coplanar photodiode of FIG. 2.

As discussed above, the predominant polarity regions 54 (p+ as shown in FIG. 2) comprise shallow bands that are wider but typically shallower than the alternating bands of opposite polarity 56 (n+ as shown in FIG. 2). Each predominant polarity region 54 is associated with a metallized electrical contact 64, and each polarity region 56 is associated with a metallized electrical contact 66. Electrical contacts 64 and 66 run the length of each polarity band 54 and 56 respectively (as better seen in FIG. 3) along wafer surface 58, and are connected at one edge of photodiode 50 respectively to anode terminal 70 and cathode terminal 72. It should be understood that the widths of electrical contacts 64 and 66 relative to bands 54 and 56 are illustrated out of proportion in FIG. 2 for purposes of illustration. Electrical contacts 64 and 66 should generally be kept as thin as possible to minimize any interference with or deflection of blue light passing between scintillating crystal 74 and photodiode 50. In FIG. 3, electrical contacts 64 and 66 are shown more accurately.

Figure 4:
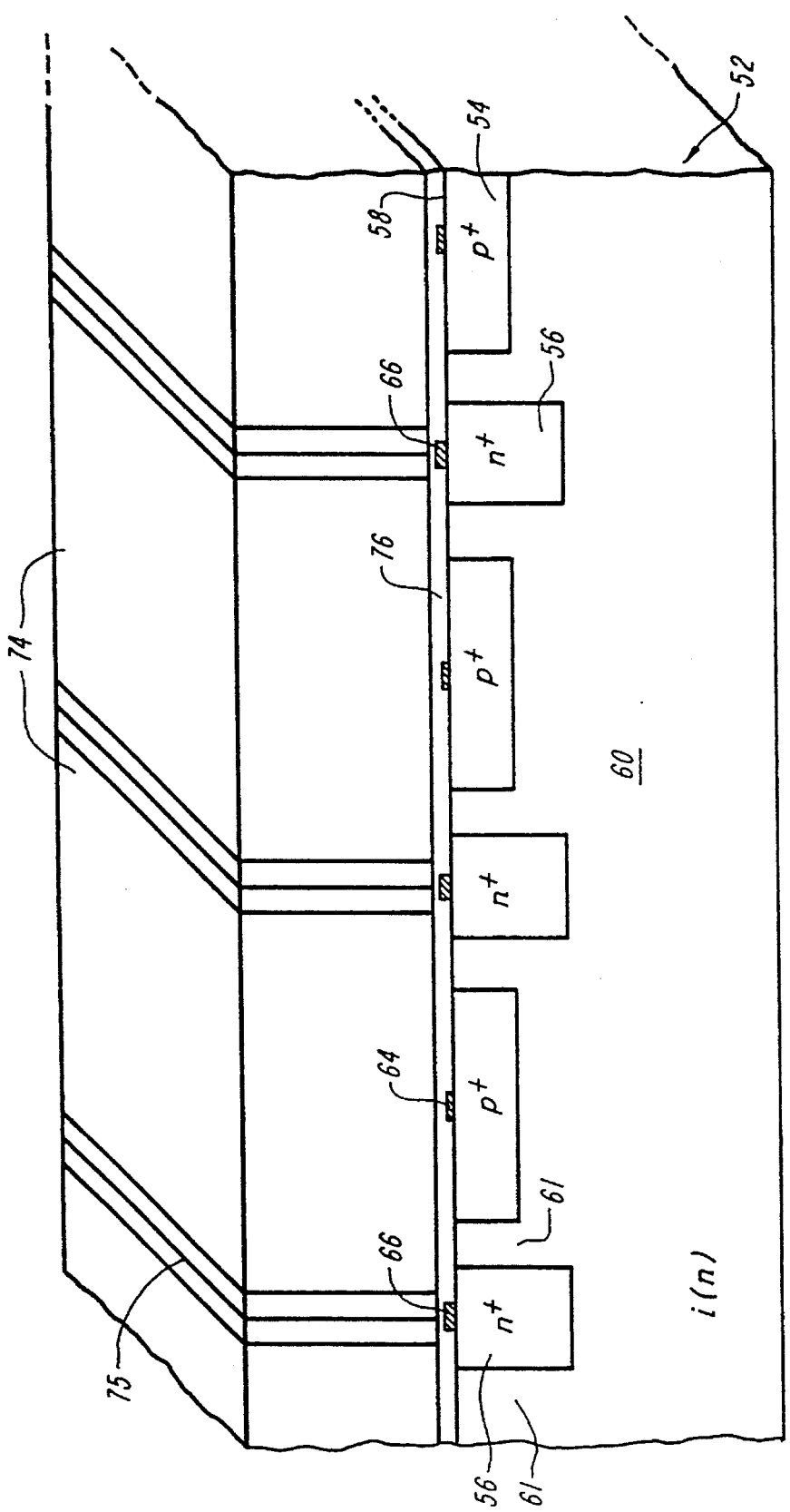
FIG. 4 is a partial perspective view of a coplanar photodiode array together with associated scintillating crystals in accordance with this invention.

In an X-ray detection system, each predominant polarity region 54 is associated with a suitable scintillating crystal, shown in dotted outline in FIG. 2 and identified by reference numeral 74. As seen in FIG. 2, in a preferred embodiment of this invention, scintillating crystal 74 is dimensioned so as to cover predominant polarity band 54 as well as the bands 61 of silicon bulk region 60 on either side of band 54, extending so as to overlap the respective adjacent opposite polarity bands 56. Scintillating crystal positioning means may be used to facilitate the positioning of each crystal relative to band 54 of its associated photodiode. For example, metallized alignment marks may be deposited on wafer surface 58 for this purpose. Scintillator crystal 74 is mounted along wafer surface 58 adjoining the surface portion of band 54 by conventional means such as silicon grease or other optically-transparent epoxy as a coupling medium. The epoxy or glue layer 76 (as shown in FIG. 4) will typically range from about 25–50 microns in thickness.

Photodiode 50 operates generally in similar fashion to conventional photodiodes, but with significantly improved results, as well as reduced manufacturing costs, owing to the optimized geometry of this construction. Thus, X-rays 78 from an X-ray source enter scintillating crystal 74, which converts the X-rays into blue light. The light photons from scintillating crystal 74 pass into the shallow P-doped region 54, penetrating only a few microns into the photodiode, where they generate electron-hole pairs. The electrical charges thus generated diffuse respectively to the p+ and n+ regions, and from there to electrical contacts 64 and 66 respectively thereby generating an electrical current proportional to the flux of the X-rays 78 absorbed into scintillating crystal 74.

In an array of side by side photodiodes, each constructed as shown in FIG. 2, bands 56 of opposite polarity flanking either side of each predominant polarity band 54 to a depth as great as or somewhat greater than the depth of band 54, act as "channel stops" that minimize electrical crosstalk and reduce erroneous readings by blocking the spillover of electrical charges between adjacent photodiodes. The distance between adjacent bands 54 and 56 of either the same or an adjacent photodiode is kept small (on the order of about 10–25 microns) relative to the width of bands 54 and 56 so as to minimize the amount of light from a scintillating crystal that activates any part of the bulk silicon zone 60. Because the channel-stop bands 56 block electrical charge spillover to adjacent channels, any secondary charge generation will likely be collected by the proper band 54 or 56. It should be understood that in FIGS. 2 and 3, the relative widths of the bands 61 of bulk silicon 60 separating alternating bands 54 and 56, as well as the depths of bands 54 and 56 relative to the overall thickness of the silicon wafer, have been exaggerated for illustrative purposes.

FIG. 3, an enlarged, schematic, sectional view of photodiode 50 along the line 3—3 of FIG. 2 better illustrates a preferred geometry for photodiodes in accordance with this invention. As seen in FIG. 3, predominant P-doped region 54 is a generally rectangular area centrally located along surface 58 (see FIG. 2) of photodiode 50. Along all four edges, rectangular P-doped region 54 is surrounded by relatively narrow bands 61 of bulk silicon region 60, thus defining a second, larger rectangle. Along all sides of that second, larger rectangle 61 of bulk silicon region 60 is a channel stop comprising N-doped region 56. The placement of a region 56 channel stop at both ends of the photodiode minimizes or eliminates electrical charge leakage associated with edge effects. It will be apparent that, in the preferred embodiment of this invention wherein the channel stop region 56 substantially completely surrounds a substantially rectangular region 54, the surrounding band 61 of bulk silicon region 60 and the channel stop region 56 will also be of a rectangular shape.

Electrical contacts 64 and 66 have been superimposed for illustrative purposes on the sectional views of P-doped region 54 and N-doped region 56. As seen in FIG. 3, electrical connections from contact 64 to the respective electrical terminal is made via a bonding pad 70 at the short side of the active zone 54. When photodiode 50 of FIG. 3 is utilized in a coplanar photodiode array of multiple, adjacent units, as illustrated in FIG. 4, a single metallization layer around the photodiodes interconnects each of the individual electrical contacts 66 in the array. It is also within the scope of this invention to utilize sheets 75 of separating material between adjacent scintillating crystals on a coplanar photodiode array, as shown in FIG. 4, to reduce optical cross-talk.

FIG. 4 illustrates an embodiment of an X-ray detection system utilizing a coplanar photodiode array in accordance with this invention. As shown in FIG. 4, silicon wafer 52 comprises a plurality of alternating P-doped (p+) regions 54 and N-doped (n+) regions 56 formed along planar surface 58 and extending into a silicon bulk (i(n)) region 60. Alternating bands of region 54 and region 56 are separated by narrow bands 61 of the silicon bulk region 60. As shown in FIG. 4, P-doped regions 54 predominate along surface 58, as seen by the relatively greater width of regions 54 as compared with N-doped regions 56. As described above in connection with FIG. 2, it will be understood that in an alternative and substantially equivalent embodiment of this invention, the predominant regions 54 may be N-doped, and regions 56 would then be P-doped.

As shown in FIG. 4, in a preferred embodiment of this invention, the non-dominant regions 56 extend into the silicon bulk region 60 to a depth greater than the depth of the predominant regions 54. Associated with each region 54 is a metallized electrical contact 64 running along the portion of region 54 adjacent surface 58. Similarly, associated with each region 56 is a metallized electrical contact 66 also running along the portion of region 56 adjacent surface 58.

Associated with each predominant region 54 is a scintillating crystal 74 glued to surface 58 with an epoxy or glue layer 76. Each scintillating crystal 74 is preferably dimensioned and positioned vis-a-vis its associated predominant region 54 so as to cover not only all of region 54 but also the entire portion of surface 58 between the bands of region 56 flanking region 54, and also so as to partially overlap the flanking bands of region 56, as seen in FIG. 4. In still another embodiment of this invention, as also shown in FIG. 4, sheets 75 of a separating material may be advantageously located between adjacent scintillating crystals 74 to reduce the scatter of light between adjacent crystals and their associated regions 54.

It has been determined that the coplanar photodiodes and photodiode arrays of this invention result in an improvement in X-ray detection of about 25% as compared with the performance of the prior art X-ray detection systems. The improvement in performance is believed to be attributable to the reduction of electrical and optical crosstalk, better charge collection, lower capacitance and faster response, all resulting from the optimized geometry of the coplanar photodiodes of this invention. In addition to the foregoing performance improvements, the coplanar photodiodes of this invention are easier, quicker, and less expensive to manufacture because all of the required process operations (namely, doping the silicon wafer and making the necessary electrical connections to the doped regions) are all performed along a single surface of the silicon wafer. Furthermore, this simplified manufacturing process lends itself to a higher degree of uniformity among the coplanar photodiodes thus insuring reproduceability of results and improving yields.

The embodiments of the present invention described are intended to be taken in an illustrative and noir a limiting sense. Various modifications and changes may be made to these embodiments by persons skilled in the art without departing from the scope of the present invention as defined in the appended claims.

What is claimed is:

1. A coplanar, non-dielectrically isolated photodiode for X-ray detection comprising semiconductor means having an absorption face and adjoining said face: (a) a single, elongated first doped region having a first polarity and defined by planar walls extending substantially perpendicularly from said absorption face into said semiconductor means to a first depth; (b) a second doped region having a polarity opposite that of said first doped region and defined by planar walls extending substantially perpendicularly from said absorption face into said semiconductor means to a second depth that is substantially equal to or greater than said first depth; (c) a substantially undoped region extending from said absorption face into said semiconductor means so as to separate and completely surround both of said first and second regions and to create a single p-n junction between said first and second doped regions; and (d) first electrical contact means connected to said first region along said absorption face.

2. Coplanar photodiode according to claim 1 further wherein the surface area of said first doped region along said face is greater than the surface area of said second doped region along said face.

3. Coplanar photodiode according to claim 2 further wherein each elongated planar wall defining said first doped region is substantially parallel to an elongated planar wall defining said second doped region.

4. Coplanar photodiode according to claim 3 further wherein said second doped region is substantially unbiased.

5. Coplanar photodiode according to claim 1 further comprising a third doped region underlying said undoped region and having the same polarity as said second doped region.

6. Coplanar photodiode according to claim 1 wherein said first depth ranges from about 1–2 microns.

7. Coplanar photodiode according to claim 6 wherein said second depth ranges from about 2–3 microns.

8. Coplanar photodiode according to claim 3 wherein said first depth ranges from about 1–2 microns and said second depth ranges from about 2–3 microns.

9. Coplanar photodiode according to claim 1 further comprising second electrical contact means connected to said second region along said absorption face.

10. Coplanar photodiode according to claim 9 wherein said second electrical contact means comprises a narrow metal strip along the surface of said second region.

11. Coplanar photodiode according to claim 1 wherein said semiconductor means comprises a silicon wafer.

12. Coplanar photodiode according to claim 2 wherein said first region is P-doped and said second region is N-doped.

13. Coplanar photodiode according to claim 2 wherein said first region is N-doped and said second region is P-doped.

14. Coplanar photodiode according to claim 2 wherein said first doped region comprises a first surface portion centrally-located on said face.

15. Coplanar photodiode according to claim 2 wherein said first doped region comprises a first substantially rectangular band centrally located along said face and said second doped region comprises a second, larger rectangular band surrounding said first rectangular band, said first and second rectangular bands being separated by bands of said undoped region.

16. Apparatus for detecting the light produced by X-rays absorbed in a scintillating crystal, said apparatus comprising non-dielectrically isolated photodiode means comprising alternating pairs of P-doped and N-doped regions, each said pair comprising a single p-n junction, wherein said doped regions extend from a single planar surface of said photodiode means into said photodiode means and associated electrical contacts for each doped region positioned along said single planar surface, further wherein said P-doped and N-doped regions are separated by a substantially undoped region extending from said planar surface into said photodiode means so as to completely surround each said P-doped and N-doped region.

17. Apparatus according to claim 16 further wherein either said P-doped or N-doped regions predominate along said planar surface.

18. In an X-ray detection system comprising in combination an X-ray source; scintillating crystal means to convert X-ray radiation into light; non-dielectrically isolated photodiode means to convert light into electrical current, said crystal means and photodiode means being mutually glued along an interface therebetween; frame means for positioning the crystal and photodiode means relative to said X-ray source; electrical conductor means for collecting electrical charges generated in the photodiode means; and electrical means for converting the electrical signals from the photodiode means into measurements of X-ray detection; the improvements comprising: adjacent said interface, alternating pairs of P-doped and N-doped regions of said photodiode means, each said pair comprising a single p-n junction, wherein each of said P- and N-doped regions is separated from one another and from adjacent P-N pairs by bands of undoped material, the less-dominant of each said doped region of a pair surrounding at least a portion of the perimeter of the associated predominant-doped region and extending into the photodiode means to a depth substantially equal to or greater than the depth of said predominant-doped region, and electrical contacts associated respectively with said P- and N-doped regions and located along said interface.

19. Apparatus according to claim 17 wherein each non-dominant doped region extends to a depth substantially equal to or greater than the depth of the associated predominant-doped region.

20. Apparatus according to claim 19 wherein said photodiode means comprises a plurality of individual photodiode units aligned in side-by-side relationship, each individual photodiode unit comprising a single pair of P-doped and N-doped regions.

21. Apparatus according to claim 20 further wherein each said photodiode unit comprises a planar photodiode surface having at least a band of predominant-doped region surrounded by undoped material which, in turn, is surrounded by non-dominant doped region.

22. Apparatus according to claim 21 further comprising an X-ray scintillating crystal associated with the predominant-doped region of each photodiode unit.

23. Apparatus according to claim 22 wherein each said scintillating crystal is glued to its associated photodiode unit along said surface of said photodiode unit.

24. Apparatus according to claim 23 wherein each said scintillating crystal is sized and positioned relative to its associated photodiode unit so as to substantially cover the portion of said surface between said bands of non-dominant doped region and to overlap each of said bands of non-dominant doped region.

25. Apparatus according to claim 23 wherein each said scintillating crystal is glued to its associated photodiode unit with an optical epoxy.

26. Apparatus according to claim 23 further comprising scintillating crystal positioning means on each photodiode unit.

27. Apparatus according to claim 26 wherein said scintillating crystal positioning means comprise metal deposit alignment marks on said surface.

28. Apparatus according to claim 17 wherein said non-dominant doped region is substantially unbiased.

29. Apparatus according to claim 17 wherein said P-doped and N-doped regions are formed in a layer of substantially undoped material.

30. Apparatus according to claim 29 further comprising another non-dominant doped region on the side opposite to said P-doped and N-doped regions.

31. Apparatus according to claim 19 wherein said predominant-doped region extends to a depth of about 1–2 microns and said non-dominant doped region extends to a depth of about 2–3 microns.

32. Apparatus according to claim 16 wherein said electrical contacts comprise narrow metal strips respectively along the surfaces of said P-doped and N-doped regions.

33. Apparatus according to claim 16 wherein said photodiode comprises a silicon wafer.

34. Apparatus according to claim 17 wherein said P-doped region predominates.

35. Apparatus according to claim 17 wherein said N-doped region predominates.

36. Apparatus according to claim 22 further comprising sheets of separating material positioned between adjacent scintillating crystals.

37. The X-ray detection system of claim 18 wherein said photodiode means comprises an array of individual photodiode units aligned in side-by-side relationship, each photodiode unit comprising a band of said predominant-doped region surrounded by undoped material which, in turn, is surrounded by non-dominant doped region.

38. The X-ray detection system of claim 37 wherein said crystal means comprises a scintillating crystal associated with the predominant-doped region of each photodiode unit.

39. The X-ray detection system of claim 38 further comprising sheets of separating material positioned between adjacent scintillating crystals.

40. The X-ray detection system according to claim 38 further wherein each said scintillating crystal is sized and positioned relative to its associated photodiode unit so as to substantially cover the portion of said surface between bands of non-dominant doped region and to overlap each of said bands of non-dominant doped region.

* * * * *